United States Patent [19]

Den Boer

[11] Patent Number: 5,287,752
[45] Date of Patent: Feb. 22, 1994

[54] MEASURMENT OF GAS AND LIQUID FLOWRATES AND WATERCUT OF MULTIPHASE MIXTURES OF OIL, WATER AND GAS

[75] Inventor: Johannis J. Den Boer, Rijswijk, Netherlands

[73] Assignee: Shell Oil Company, Houston, Tex.

[21] Appl. No.: 872,377

[22] Filed: Apr. 23, 1992

[30] Foreign Application Priority Data

Apr. 26, 1991 [GB] United Kingdom ............... 9109074.6

[51] Int. Cl.⁵ .................................................. G01F 1/74
[52] U.S. Cl. .................................................. 73/861.04
[58] Field of Search ............ 73/861.04, 861.06, 861.05

[56] References Cited

U.S. PATENT DOCUMENTS 4,751,842  6/1988  Ekrann et al. ................... 73/861.06
4,975,645 12/1990  Lucas ................................ 73/861.04

*Primary Examiner*—Herbert Goldstein

[57] ABSTRACT

A device and method for measuring multiphase flow in a pipeline with an electric measurement system which includes a plurality of capacitors, which capacitors are formed of at least two plates of non-conducting material, each plate being provided with an array of electrodes. The plates are arranged in the interior of the pipeline and extend substantially parallel in the longitudinal direction thereof.

The liquid and gas flowrates are gauged by continuously measuring both the velocity and cross-sectional area of the pipeline occupied by each phase.

7 Claims, 4 Drawing Sheets

MEASUREMENT OF GAS AND LIQUID FLOWRATES AND WATERCUT OF MULTIPHASE MIXTURES OF OIL, WATER AND GAS

FIELD OF THE INVENTION

The present invention relates to a method and apparatus for measuring gas and liquid flowrates and/or watercut of multiphase mixtures of oil, water and gas flowing through a pipeline from a well.

BACKGROUND OF THE INVENTION

In conventional multiphase flow-metering, gas and liquid phases in a pipeline are separated in test separators. However, test separators are too expensive to install on a one per well basis. One test separator is usually installed at each production station and each well is produced over the separator when it is felt that a measurement of the well flowrate is essential. In practice this means that the flow from each well is only measured once per month and then only for a period of just one day. Test separators also suffer from a range of problems: they can be difficult to control, turndown is limited, they are bulky and can be non-representative because they only sample the flowrate for part of the production time of a well. For marginal fields, the cost of such separators can even make the development uneconomical so they are left out and the actual well flowrates are not measured.

SUMMARY OF THE INVENTION

It is therefore an object of the invention to provide a method and apparatus for directly measuring the flowrate of each component in an oil/water/gas mixture flowing together in a pipeline without the need to separate the phases.

It is another object of the invention to provide a compact solution to the multiphase measurement problem and to provide an economical technique to achieve a continuous measurement of production from a single well.

It is still another object of the invention to provide a method and apparatus for multiphase measurement in a pipeline, which could permanently be carried out or installed in individual flow lines or in a local test manifold, making long and expensive test lines to satellite wells obsolete.

The invention therefore provides a method for determining the liquid and gas flowrates and/or the watercut of multiphase mixtures of oil, water and gas flowing through a horizontal or inclined pipeline in an intermittent type of flow, characterized by the steps of locating a pair of non-moving parallel plates inside the horizontal pipe in line with the flow, the plates being positioned in the vertical plane and at least one of the plates comprising a plurality of segmented electrodes, the segments of an electrode being located one below another, thus forming a nxm matrix of n columns and m rows of capacitor plates (n,m = 1,2,3, . . . ), and the other plate of the pair comprising at least one continuous electrode, arranged in such a manner that a segmented electrode on the first plate and the electrode on the second plate form a capacitive sensor that gives a signal related to the mixture of oil, water and gas that happens to be between the electrodes; measuring by impedance the level of the liquid to gas interface in the pipeline and the void fraction across the whole cross-section of the pipeline, the measuring being obtained from a single column of sensors; continuously measuring the flow pattern velocity by timing the passage of the disturbances within the flow patterns between matrix segments located on a same row near the top of the pipeline; continuously measuring liquid phase velocity between matrix segments located on the same level or row by cross-correlating the variations in impedance between them; and deriving from the above measured quantities the flowrates for both the liquid and the gas.

Advantageously, the method of the invention comprises the additional step of measuring the watercut in the liquid filled part of the pipeline by calculating the dielectric constant of the fluid between the plates from the capacitance measurement.

The invention also provides an apparatus for determining the liquid and gas flowrates and the watercut of multiphase mixtures of oil, water and gas flowing through a horizontal or inclined pipeline in an intermittent type of flow, characterized by a pair of non-moving parallel plates inside the horizontal pipe in line with the flow, the plates being positioned in the vertical plane and at least one of the plates comprising a plurality of segmented electrodes, the segments of an electrode being located one below another, thus forming a nxm matrix of n columns and m rows of capacitor plates (n,m +1,2,3, . . . ), and the other plate of the pair comprising at least one continuous electrode, arranged in such a manner that a segmented electrode on the first plate and the electrode on the second plate form a capacitive sensor that gives a signal related to the mixture of oil, water and gas that happens to be between the electrodes, means for measuring by impedance the level of the liquid to gas interface in the pipeline and the void fraction across the whole of the pipeline; means for continuously measuring the flow pattern velocity by timing the passage of the disturbances within the flow patterns between matrix segments located on a same row near the top of the pipeline; means for continuously measuring liquid phase velocity between matrix segments located on same level or row by correlating the variations in impedance between them; means for measuring the watercut in the liquid filled part of the pipeline by calculating the dielectric constant of the fluid between the plates from the impedance measurement; and means for deriving from the above measured quantities the flowrates for both the liquid and the gas.

The principle of the invention is based upon the fact that during multiphase flow in a pipeline, the distribution of the liquid and gas phases across the pipeline is not homogeneous; it varies with time even for a fixed flowrate of liquid and gas.

At different flowrates the distribution changes considerably and various flow regimes can be identified. Multiphase flow refers to the flow of both a gas and liquid phase down a pipe at the same time where the liquid phase is made up of two components, oil and water.

DESCRIPTION OF THE DRAWINGS

The invention will now be described in more detail by way of example by reference to the accompanying drawings, in which.

DESCRIPTION OF PREFERRED EMBODIMENTS

Figure 1:
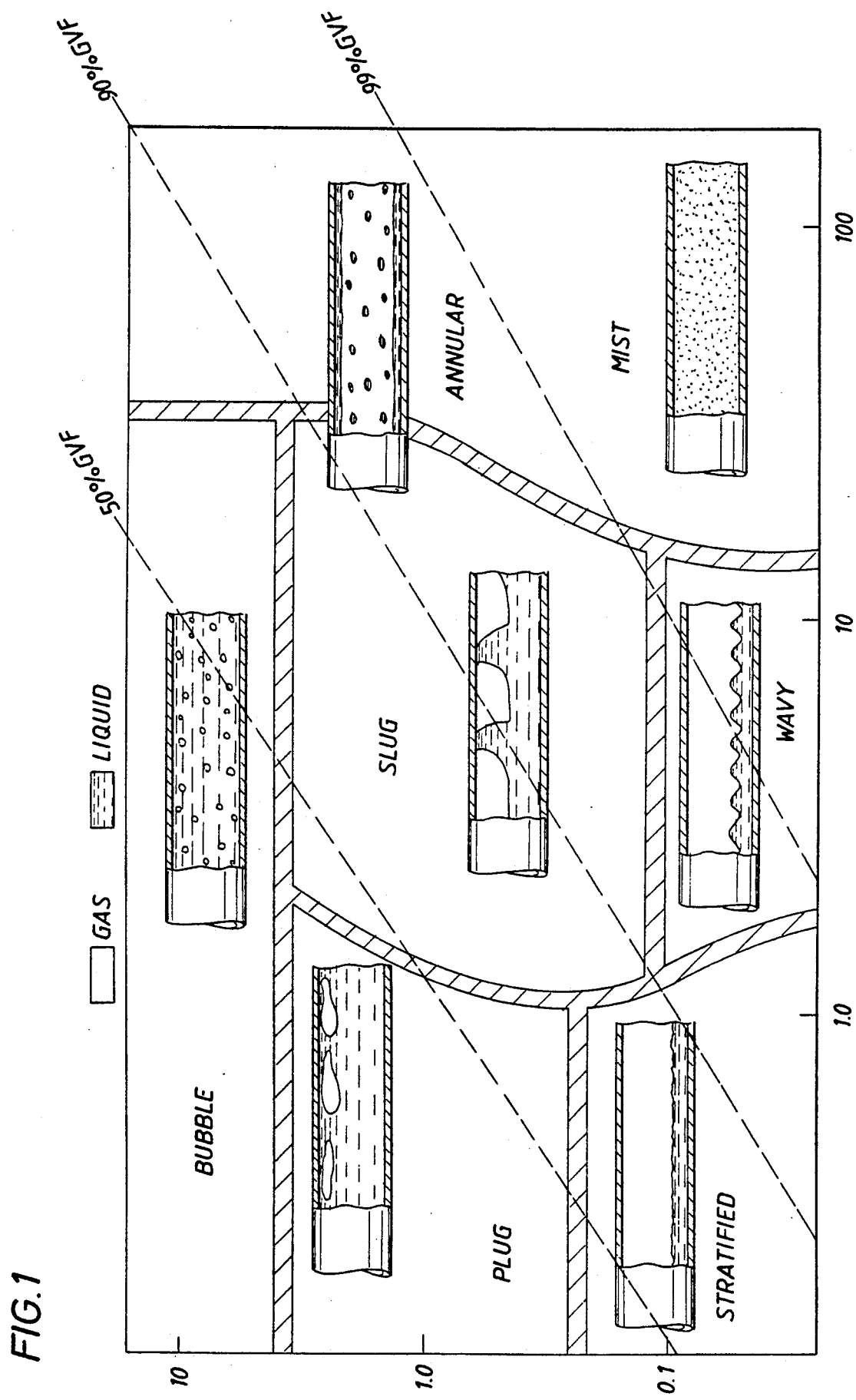
FIG. 1 represents several flow patterns in a pipeline for horizontal multiphase flow.

Referring now to FIG. 1, a flow pattern map of various flow regimes for a horizontal multiphase flow in a pipeline has been shown.

The horizontal axis represents the superficial gas velocity in m/s, whereas the vertical axis represents the superficial liquid velocity in m/s.

The dashed lines represent percentage of gas volume fraction (GVF).

The black portions in a pipeline represent liquid, whereas the white portions in a pipeline represent gas. In FIG. 1 the following flow regimes are represented: bubble, plug, slug, annular, stratified, wavy and mist.

Typically, the flow regimes are described by the way they appear in the pipeline; stratified flow has two distinct layers, one liquid and one gas; in slug flow, the cross-section of the pipeline is first filled with gas, then liquid, then gas etc.

The flow regimes normally encountered in a pipeline are stratified, slug, plug, bubble and annular.

Figure 2:
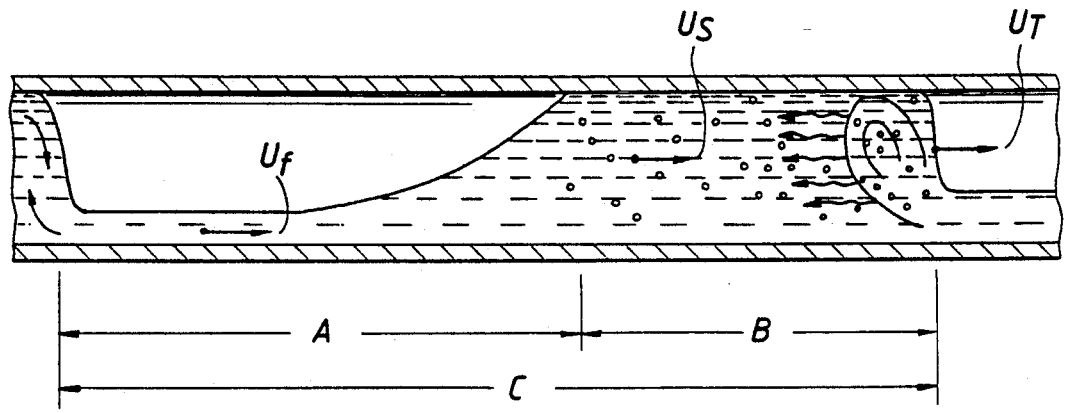
FIG. 2 represents a model of an intermittent type of flow in a horizontal pipe.

FIG. 2 shows a model of an intermittent type of flow. The arrow A represents a film; the arrow B represents a slug and the arrow C represents a slug unit.

The method and apparatus of the invention operate advantageously in the intermittent flow regime.

In practice this is not a limitation because, in almost all practical applications, the gas and liquid are flowing in the intermittent regime.

According to the invention the liquid and gas flowrates are gauged by continuously measuring both the velocity of each phase and the cross-sectional area of the pipe occupied by each phase.

Taking the liquid first, the total flow in a time T can be simply expressed as $$\int_0^T u(t)R(t)A\,dt \quad (1)$$

where u(t) is the liquid velocity at time t,

R(t) is the fractional liquid holdup at time t, i.e. the fraction of the pipe's cross-sectional area that is occupied by liquid and A is the cross-sectional area of the pipe.

Slug flow is normally described in two parts, a slow-moving liquid film which only partly fills the pipe, and a fast moving liquid slug which totally fills the pipe but only for a short while. Splitting equation 1 into these parts and considering it over the repetition interval of the slugs gives the liquid flow rate, $Q_1$ $$Q_1 = \frac{1}{T_s + T_f} \int_0^{T_s + T_f} u(t)R(t)A\,dt \quad (2)$$

where $T_s$ is the time taken for the slug to pass and $T_f$ is the time taken for the film to pass.

Solving the integral yields two parts, one for the film and one for the slug $$Q_1 = (u_s T_s R_s + u_f T_f R_f)\frac{A}{T_s + T_f} \quad (3)$$

where $u_s$ is the liquid velocity in the slug, $R_s$ is the liquid hold-up in the slug, $u_f$ is the liquid velocity in the film and $R_f$ is the liquid hold-up in the film.

The gas is transported between the slugs in the area above the liquid film and in the slug as gas bubbles entrained in the liquid. A similar approach to that used for the liquid flowrate gives two parts to the gas flowrate, $Q_g$:

$$Q_g = (u_s T_s(1 - R_s) + u_T T_f(1 - R_f))\frac{A}{T_s + T_f} \quad (4)$$

where $u_T$ is the slug velocity i.e. the velocity with which the slug travels down the pipe. Again, the invention measures all these parameters.

Figure 3:
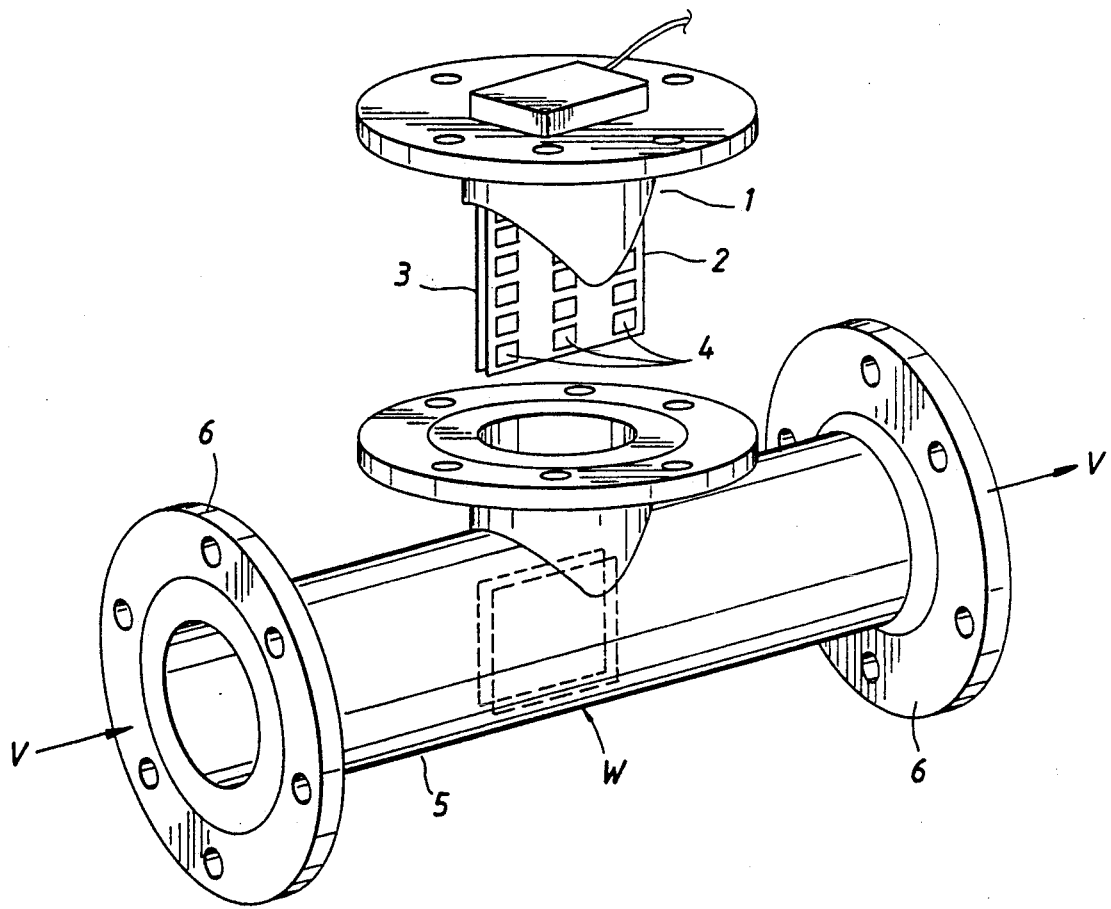
FIG. 3 represents a configuration of a multicapacitance multiphase flow meter of the invention.

FIG. 3 represents a configuration of the multicapacitance multiphase flowmeter of the invention.

The measuring section (1) comprises a spool piece housing two plates (2,3) in line with the flow and etched on one of these plates (2) is a number of segmented electrodes 4 forming a nxm matrix of capacitors (n,m =1,2,3 . . . , indicating n columns and m rows in the matrix). The plate (3) is provided with at least one continuous electrode (not shown for reasons of clarity).

The meter has been shown extracted from the pipeline (5), whereas the dashed lines W show the position of the measuring electrodes in the flowline (5). The arrows V represent the direction of flow. The flowline 5 is provided with flanges (6) for suitable mechanical connection to the flowline.

Figure 4:
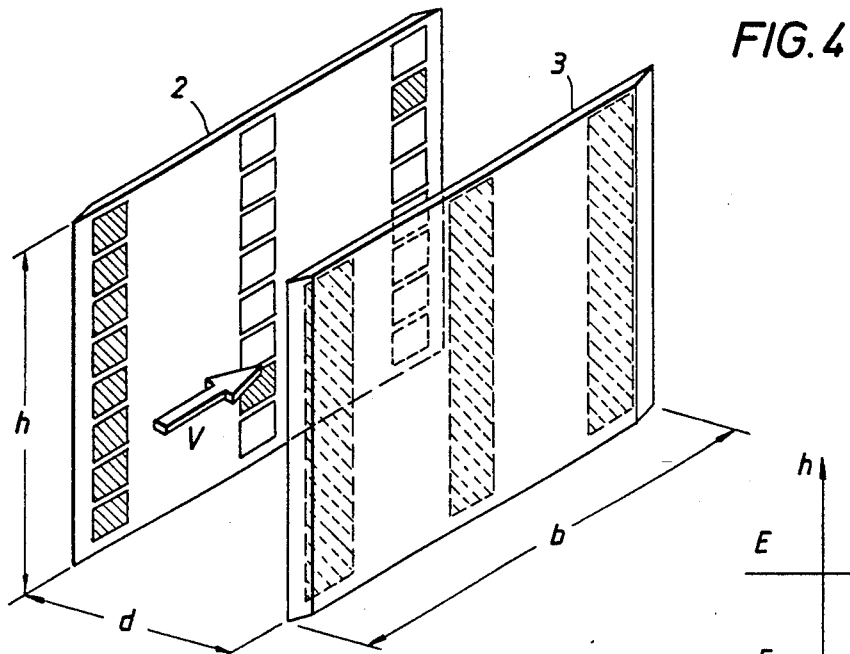
FIG. 4 represents a multicapacitance flow meter sensor configuration of the invention.

FIG. 4 shows further details of the sensor configuration of FIG. 3.

In this case the number of rows on the first plate 2 is eight, whereas the number of columns on the first plate is three.

Three vertical columns of electrodes forming three columns of eight capacitor plates have been shown on the first plate 2.

However, it will be appreciated that any suitable nxm matrix is applicable. A typical arrangement is shown in FIG. 4 where each of the eight capacitor plates per column on the first plate 2 forms a capacitor with the continuous electrodes on the other plate 3. The impedance measured by each capacitor is a function of the dielectric constant and conductivity of the fluid filling the gap between its electrodes and these in turn are dependent on the actual mixture of oil, water and gas in the gap. If water fills the gap then the measured capacitance is small and the conductance is high. As the amount of oil increases and an oil/water emulsion is formed, the conductance reduces and the capacitance increases to a large value. Oil alone gives a low conductance and a capacitance between the water and emulsion figure. Gas alone gives a low conductance and a capacitance between the oil and water figure. Suitable dimensions are a height h of 10 cm, a width b of 17 cm and a distance d of 1 cm.

In another advantageous embodiment of the invention, the width b is 4 cm and there is one continuous electrode covering all the columns of segments. The variation in dielectric constant F is shown schematically in FIG. 5 the horizontal axis of which represents the dielectric constant whereas the vertical axis represents the height h.

The basic parameters that can be obtained from the measurements by the capacitors are the level of the liquid to gas interface in the pipe, the void fraction across the whole of the pipe, the velocity of the intermittent flows, the velocity of the liquid phase and the watercut in the liquid filled part of the pipe. The liquid level and void fraction (applicable in the slug, plug, bubble and stratified flow regimes) are obtained from a single column of capacitors by comparing the value of measured impedance to that expected with gas between the plates. The intermittent flow velocity is measured by timing the disturbances within the intermittent flows between capacitors on the same row near the top of the pipe and the liquid velocities are measured between capacitors on the same level or row by correlating the variations in impedance between them. These variations are caused by the turbulent nature of multiphase flow and the correlation effectively measures the time it takes for the liquid to travel from one capacitor to the next. In principle the watercut can be determined by calculating the dielectric constant of the fluid between the plates from the capacitance measurements — there is a direct relationship between the dielectric constant of an oil/water mixture and the ratio of the water in the oil. All the impedance measurements are made continuously.

Figure 5:
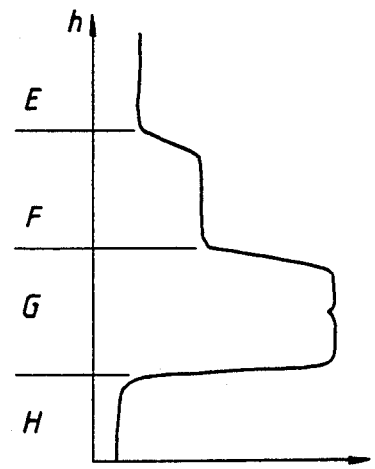
FIG. 5 represents the principle of the operation of the method of the invention.

In FIGS. 5 E, F, G and H represent the flow of gas only, oil only, oil continuous emulsion (water cut <40%) and water continuous emulsion (water cut >40%) respectively.

FIGS. 6a–e show a typical set of the signals used to give the level (FIG. 6a) and velocity (FIGS. 6b–e) measurements for the passage of a few slugs. At the left hand side of FIGS. 6a–e the flowline 5 provided with a measuring section 1 has been represented. The flow direction has been represented by the arrow V.

Figure 6A:
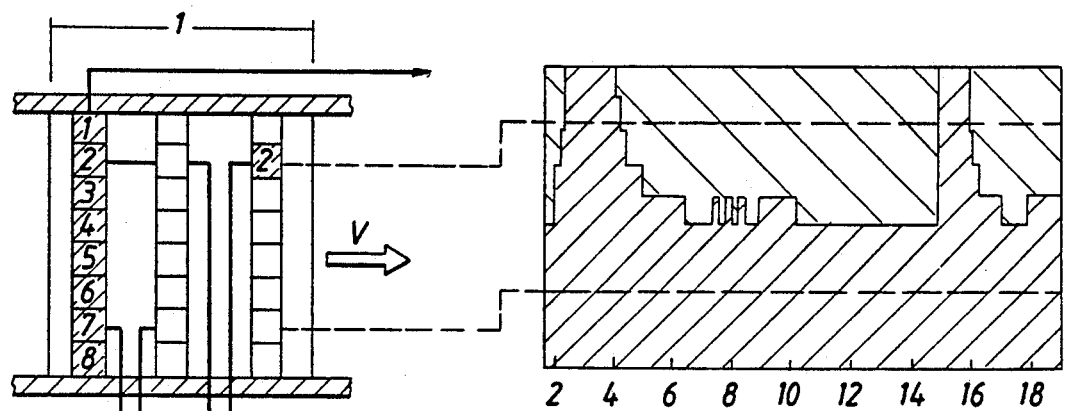
FIGS. 6a–e represent typical signals from the multicapacitance flow meter of the invention.
Figure 6B:
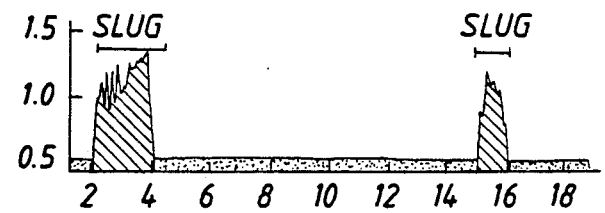
Figure 6C:
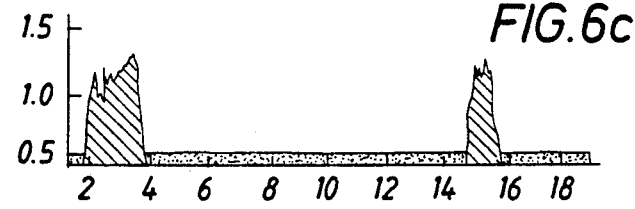
Figure 6D:
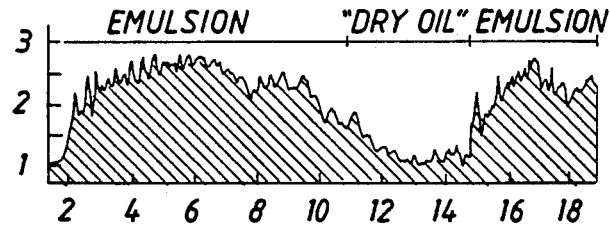
Figure 6E:
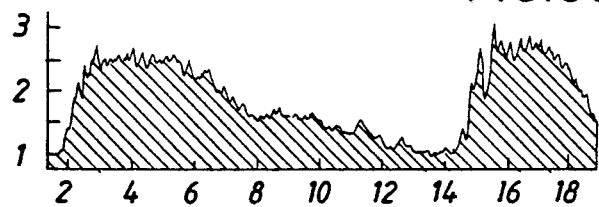

In FIG. 6a the vertical axis represents level (in cm), whereas the horizontal axis represents time (in seconds).

In FIGS. 6b–e the vertical axes represent admittance (in volts), whereas the horizontal axes represent time (in seconds).

The physical measurements have to provide the data for equations 3 and 4. Repeating the equation for the liquid flow $$Q_l = (u_s T_s R_s + u_f T_f R_f) \frac{A}{T_s + T_f} \quad (3)$$

the parameters that need continuous measurement are the cross-section occupied by the liquid ($R_s$ and $R_f$), the velocity with which the liquid travels ($u_s$ and $u_f$) and whether a slug is passing or not ($T_s$ and $T_f$).

Taking first the liquid area, this is measured using just one column of capacitors. This differs from the conventional interface type measurement using capacitor arrays because it is not adequate to look for one gas/liquid interface. During the passage of intermittent flow, e.g. a slug, much gas becomes entrained in the liquid and therefore a method is needed that measures the actual ratio of liquid to gas at the level of each plate. This can be done quite simply if the impedance for both the liquid and gas is known, it is simply a case of comparing the measurement to the reference values and interpolating to find the ratio. Although the gas impedance is constant, changes in watercut significantly change the impedance of the liquid and it is necessary to provide compensation for this. The method chosen is to assume that over a long measuring period, say 20 seconds, at least one plate will have been completely covered by liquid. In the case of an oil external liquid emulsion, when a plate is completely covered the measured capacitance will be a maximum. This maximum is then used to calculate the void fraction at each plate. In the water external phase, the covered plate will have the greatest conductance and the same principle can be used.

The liquid velocities are measured by correlating the signals from matrix segments located in the same row. In principle the velocity at each row of capacitors is needed but this appears to be unnecessary for the limited accuracy needed to monitor well production — a single row near the bottom of the pipe gives a sufficiently representative velocity for both the liquid film velocity ($u_f$) and the liquid velocity in the slug ($u_s$).

The passage times of the slug and film are determined from the sensor plates near the top of the pipe. If the liquid reaches the top of the pipe, a slug is passing. If the liquid/gas interface is below the top of the pipe, the liquid film is passing.

Examining the equation for the gas flow, $$Q_g = (u_s T_s (1 - R_s) + u_T T_f (1 - R_f)) \frac{A}{T_s + T_f} \quad (4)$$

Only one further parameter is needed to measure the gas flow, the slug translational velocity, $u_T$. This is determined by measuring the difference in time between the arrival of a slug at the first column of capacitors and one of the subsequent columns.

Figure 7:
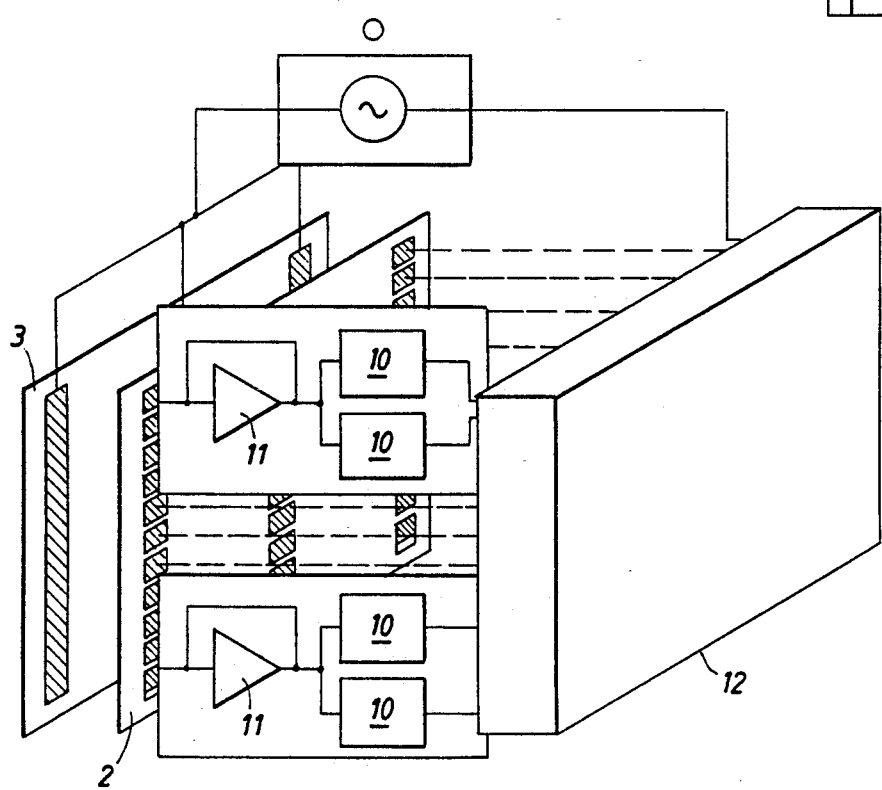
FIG. 7 represents schematically an embodiment of the signal processing system of the invention.

A simple schematic of the measurement electronics and signal processing system used in the prototype is given in FIG. 7. All the capacitors are exited by the same sine wave signal applied to the continuous electrodes by an oscillator O. Each individual capacitor is then connected to two phase sensitive detectors 10 via a charge amplifier 11 to provide signals proportional to the admittance between the capacitor plates. One detector gives a signal proportional to the susceptance between the plates of the electrodes and the other a signal proportional to the conductance.

The signals are then further processed in a dedicated processing unit 12 to give the parameters required for input to the flow model (equations 3 and 4) and subsequent calculation of the liquid and gas flowrates.

In a more advantageous embodiment of the invention a 2×8 matrix of capacitor plates is applied.

Various modifications of the present invention will become apparent to those skilled in the art from the foregoing description and accompanying drawings. Such modifications are intended to fall within the scope of the appended claims.

What is claimed is:

1. A method for determining liquid and gas flowrates and/or watercut of multiphase mixtures of oil, water and gas flowing through a horizontal or inclined pipeline in an intermittent type of flow, comprising a) locating a pair of stationary/parallel plates inside the horizontal pipe in line with the flow, said plates being positioned in the vertical plane and at least one of said plates comprising a plurality of segmented electrodes, the segments of an electrode being located one below another to form a nxm matrix of n columns and m rows of capacitor plates and the other plate of said pair comprising at least one continuous electrode, arranged in such a manner that a segmented electrode on the first plate and the electrode on the second plate form a capacitive sensor that gives a signal related to the mixture of oil, water and gas that happens to be between the electrodes;

b) measuring by impedance the level of the liquid to gas interface in the pipeline and the void fraction across the whole cross-section of the pipeline, the measuring being obtained from a single column of sensors;

c) continuously measuring the intermittent flow velocity by timing the passage of disturbances within the flow patterns between matrix segments located on a same row near the top of the pipeline;

d) continuously measuring liquid phase velocity between matrix segments located on the same level or row by cross-correlating the variations in impedance between them; and e) deriving from the above measuring quantities the flowrates for both the liquid and the gas.

2. The method as claimed in claim 1, characterized by the step of measuring the watercut in the liquid filled part of the pipeline by calculating the dielectric constant of the fluid between the plates from the capacitance measurement.

3. An apparatus for determining liquid and gas flowrates and/or watercut of multiphase mixtures of oil, water and gas flowing through a horizontal or inclined pipeline in an intermittant type of flow, characterized by a pair of stationary parallel plates inside the horizontal pipe in line with the flow, said plates being positioned in the vertical plane and at least one of said plates comprising at least one segmented electrode, the segments of the electrode being located one below another, thus forming a nxm matrix of n columns and m rows of capacitor plates and the other plate of said pair comprising at least one continuous electrode, arranged in such a manner that a segmented electrode on the first plate and the electrode on the second plate form a capacitive sensor that gives a signal related to the mixture of oil, water and gas that happens to be between the electrodes means for measuring by impedance the level of the liquid to gas interface in the pipeline and the void fraction across the whole of the pipeline; means for continuously measuring the intermittent flow velocity by timing the passage of disturbance within the flow patterns between matrix segments located on a same row near the top of the pipeline; means for continuously measuring liquid phase velocity between matrix segments located on a same level or row by correlating the variations in impedance between the segments; means for measuring the watercut in the liquid filled part of the pipeline by calculating the dielectric constant of the fluid between the plates from the impedance measurement; and means for deriving the flowrates for both the liquid and the gas.

4. The apparatus as claimed in claim 3 characterized by an array of capacitive sensors comprising of two vertical parallel plates of non-conductive material, located in line with the flow and a plurality of electrodes etched on the sensors.

5. The apparatus as claimed in claim 3 characterized by a 2×8 matrix of capacitor plates.

6. The apparatus as claimed in claim 3 characterized in that the flowrates of gas and liquid and the watercut are derived from signals produced by the matrix.

7. The apparatus as claimed in claim 3 characterized by a spool piece of a length similar to the pipeline diameter.

* * * * *